United States Patent
Guthart

(10) Patent No.: US 9,962,493 B2
(45) Date of Patent: May 8, 2018

(54) DUAL-DOSE SYRINGE SYSTEM

(71) Applicant: Frank Guthart, Plainview, NY (US)

(72) Inventor: Frank Guthart, Plainview, NY (US)

( * ) Notice: Subject to any disclaimer, the term of this patent is extended or adjusted under 35 U.S.C. 154(b) by 0 days. days.

(21) Appl. No.: 15/478,006

(22) Filed: Apr. 3, 2017

(65) Prior Publication Data

US 2017/0281872 A1    Oct. 5, 2017

Related U.S. Application Data

(60) Provisional application No. 62/316,770, filed on Apr. 1, 2016.

(51) Int. Cl.
*A61M 5/315*    (2006.01)

(52) U.S. Cl.
CPC .... *A61M 5/31501* (2013.01); *A61M 5/31511* (2013.01); *A61M 5/31593* (2013.01); *A61M 2005/31508* (2013.01)

(58) Field of Classification Search
CPC .......... A61M 5/31501; A61M 5/31593; A61M 5/31511; A61M 5/31508; A61M 5/31506; A61M 2005/3139; A61M 5/14546; A61M 2005/14553

See application file for complete search history.

(56) References Cited

U.S. PATENT DOCUMENTS

| | | | | |
|---|---|---|---|---|
| 4,367,738 A * | 1/1983 | Legendre | ............ | A61M 5/5013 604/110 |
| 5,318,544 A * | 6/1994 | Drypen | ............... | A61M 5/3155 604/210 |
| 5,925,032 A * | 7/1999 | Clements | ................ | A61M 5/34 604/192 |
| 2014/0303565 A1 * | 10/2014 | Kubo | .................... | A61M 15/08 604/208 |

* cited by examiner

*Primary Examiner* — Andrew Gilbert
*Assistant Examiner* — Hamza Darb

(57) ABSTRACT

An dual-dose syringe system is an apparatus that includes a tubular housing and a plunger. The tubular housing attaches onto a variety of syringe and needle assemblies and mounts the plunger within the syringe. The tubular housing prevents the plunger from simply traversing into the syringe. The tubular housing includes a first lateral-half portion and a second lateral half-portion that snaps onto each other and encloses a syringe. The tubular housing further includes a key slot that engages the plunger. The plunger includes a plurality of cross bars that predetermine two doses. Each of the plurality of cross bars is positioned perpendicular to a corresponding adjacent bar, forcing a user to purposefully twist the plunger in order to administer a dose. The apparatus further includes at least one spring-loaded barb that prevents the reuse of the apparatus.

5 Claims, 8 Drawing Sheets

DUAL-DOSE SYRINGE SYSTEM

The current application claims a priority to the U.S. Provisional Patent application Ser. No. 62/316,770 filed on Apr. 1, 2016. The current application is filed on Apr. 3, 2017 while Apr. 1, 2017 was on a weekend.

FIELD OF THE INVENTION

The present invention relates generally to a syringe that provides multiple doses of a drug. More specifically, the present invention safely provides dual dosages of a drug and prevents the reuse of the syringe.

BACKGROUND OF THE INVENTION

The use of syringes is the main method of providing a drug to a patient. A syringe must be used properly in order to safely and effectively provide a drug to a patient. The user may not know how to accurately provide the correct dosage to the patient with a syringe. Consequently, the patient may not receive enough medication. Receiving the incorrect dosage may result in harmful or even fatal effects for the patient.

It is therefore an objective of the present invention to provide a syringe system that controls the delivery of dosage. The present invention further provides a second dose if the initial dosage of a drug does not provide relief. The present invention prevents misuse, such that the present invention locks and prevents reuse. A variety of syringes and needles may be engaged with the present invention so that the present invention is not limited to any type of syringe or needle.

DETAILED DESCRIPTION OF THE INVENTION

All illustrations of the drawings are for the purpose of describing selected versions of the present invention and are not intended to limit the scope of the present invention.

Figure 1:
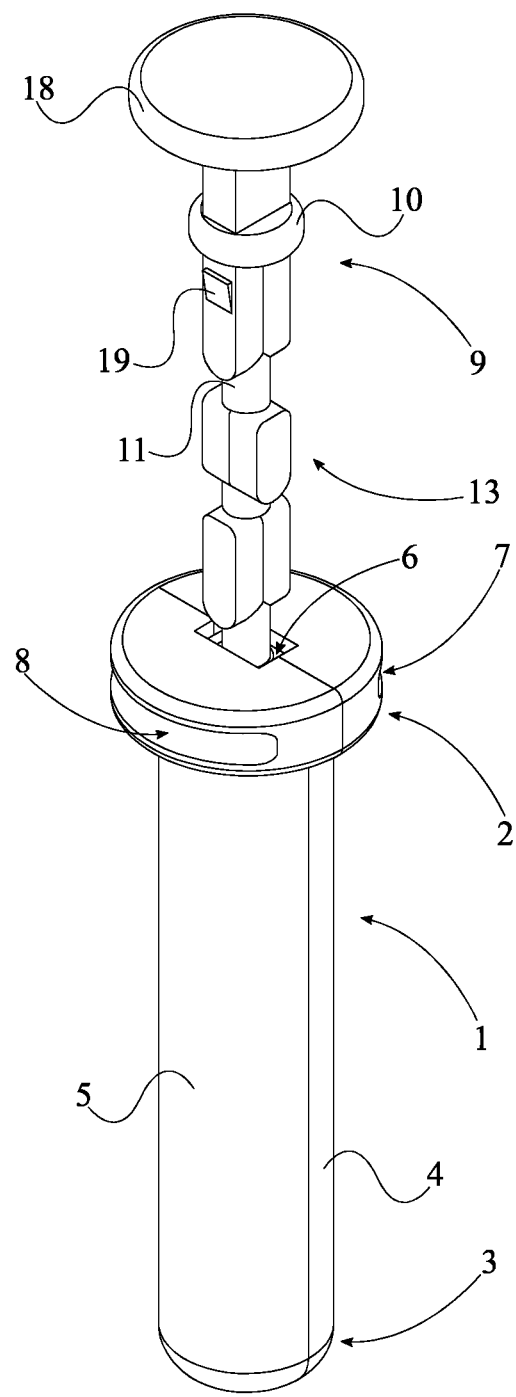
FIG. 1 is a top perspective view of the present invention, wherein the plunger is fully retraced out of the tubular housing.

The present invention is a dual-dose syringe system that accurately and safely delivers a drug to a patient. The present invention prevents reuse, eliminating the improper delivery of a drug to a patient. As illustrated in FIG. 1, the present invention comprises a tubular housing 1 and a plunger 9. The tubular housing 1 attaches to a variety of syringe and needle assemblies. The tubular housing 1 also mounts the plunger 9 within the syringe. The plunger 9 expels the drug within an engaged syringe and needle assembly. The plunger 9 defines the amount of drug expelled in each dose and engages with the tubular housing 1 such that the user does not need to measure the dosages in order to deliver the correct dosages to the patient. The amount of each dose expelled by the plunger 9 is not limited to a single amount and may vary according to the drug contained within a corresponding syringe and needle assembly.

In order for the present invention to be a universal attachment for a variety of syringe and needle assemblies, the tubular housing 1 comprises a closed end 2, an open end 3, a first lateral half-portion 4, a second lateral half-portion 5, and a key slot 6. The closed end 2 prevents the syringe within the tubular housing 1 from escaping. The open end 3 allows the needle to traverse through the tubular housing 1. The first lateral half-portion 4 and the second lateral half-portion 5 surrounds the syringe. The key slot 6 allows the plunger 9 to traverse into the tubular housing 1. In addition, the plunger 9 comprises a stopper 10, a shaft 11, a sealing body 12, and a plurality of cross bars 13. The stopper 10 prevents the plunger 9 from sliding within the syringe after both doses have been expelled. The shaft 11 positions the stopper 10, the sealing body 12, and the plurality of cross bars 13. The shaft 11 allows a user to expel the drug within the syringe without coming into contact with or contaminating the drug. The sealing body 12 pushes the drug out of the syringe. The sealing body 12 prevents any air from entering the cavity defined by the engagement between the sealing body 12 and the syringe so that the drug within the cavity does not retain any air bubbles. The plurality of cross bars 13 locks and unlocks the present invention in between dosage deliveries.

The overall configuration of the aforementioned components allows a user to deliver two accurate doses to a patient without having to measure the doses and serves as a universal attachment to syringe and needle assemblies. In order to accommodate a variety of syringe and needle assemblies, while preserving the structure and position of the key slot 6, the first lateral half-portion 4 and the second lateral half-portion 5 are detachably attached to each other, as shown in the exploded view of FIG. 8. In the preferred embodiment of the present invention, the first lateral half-portion 4 and the second lateral half-portion 5 snap onto each other. The key slot 6 traverses through the closed end 2 along the central axis 25 of the tubular housing 1 so that the plunger 9 is centrally positioned within the tubular housing 1 and consequently engage a syringe. This configuration is shown in the cross-section view of FIG. 7. The shaft 11 is slidably engaged through the key slot 6, which centrally positions the sealing body 12 within the syringe and thereby preventing any air from entering the cavity between sealing body 12 and the syringe. The sealing body 12 is positioned within the tubular housing 1 and terminally connected to the shaft 11 so that the sealing body 12 is housed within the syringe. The stopper 10 is connected along the shaft 11, offset from the sealing body 12, which allows the plurality of cross bars 13 to traverse past the key slot 6 and preventing the plunger 9 from further traversing into the syringe past the delivery of the second dose. The stopper 10 is shown preventing the plunger 9 from further traversing through the tubular housing 1 in FIG. 4.

In order to prevent inaccurate dosage delivery, each of the plurality of cross bars 13 is connected perpendicular to the shaft 11 such that each cross bar 13 does not accidentally slip past the key slot 6. The plurality of cross bars 13 is distributed along the shaft 11 between the sealing body 12 and the stopper 10 allowing sealing body 12 to traverse through the syringe and expel the drug via the needle. The distribution of the plurality of cross bars 13 along the shaft 11 predetermines the amount of each does so that the user does administer an inaccurate dose. In the preferred embodiment of the present invention, the plurality of cross bars 13 is centrally positioned with the shaft 11 to facilitate the rotation of the plunger 9 about the key slot 6. Each of the plurality of cross bars 13 comprises a round lateral portion 17. The round lateral portion 17 is oriented towards the sealing body 12 in order to facilitate both the rotation and downward movement of each of the plurality of cross bars 13. Furthermore, the plurality of cross bars 13 and the key slot 6 are coextensive, facilitating the passage of the plurality of cross bars 13 through tubular housing 1. More specifically, each of the plurality of cross bars 13 is positioned perpendicular to a corresponding adjacent bar 13 from the plurality of cross bars 13 in order to forcing the user to rotate the plunger 9 and the drug is not accidentally expelled from the needle.

Figure 5:
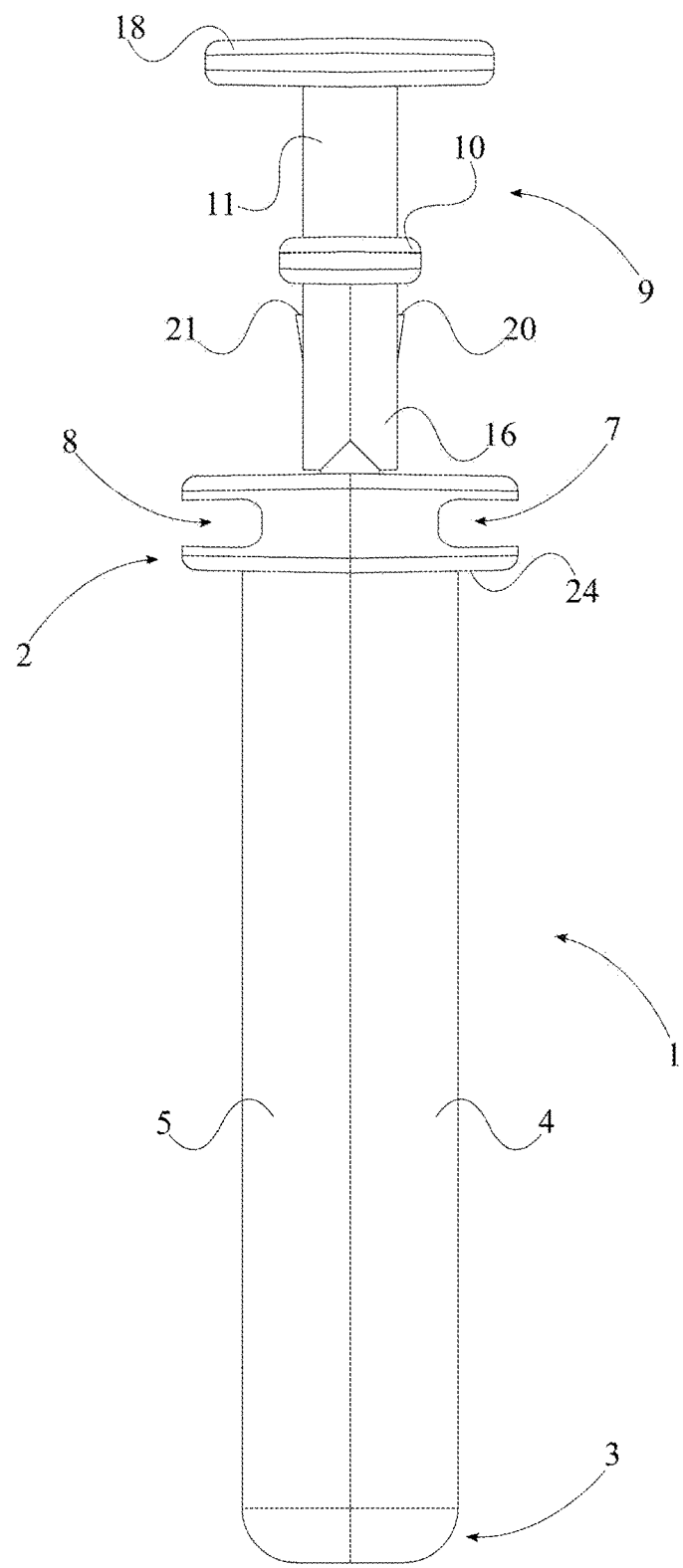
FIG. 5 is a side view of the present invention, wherein the plunger is locked within the tubular housing.

In order to effectively house a variety of syringe and needle assemblies, the tubular housing 1 further comprises a first flange-receiving hole 7 and a second flange-receiving hole 8, as shown in FIG. 5. The first flange-receiving hole 7 and the second flange-receiving hole 8 allows the flanges of the syringe to traverse through the tubular housing 1 and allows the tubular housing 1 to completely surround the syringe and needle assembly. The first flange-receiving hole 7 traverses into the first lateral half-portion 4, adjacent to the closed end 2. Similarly, the second flange-receiving hole 8 traverses into the second lateral half-portion 5, adjacent the closed end 2. This configuration accommodates the general structures of a variety of syringe and needle assemblies. More specifically, the first flange-receiving hole 7 and the second flange-receiving hole 8 are positioned perpendicular to the central axis 25 of the tubular housing 1 and diametrically opposed to each other about the tubular housing 1 as many syringe and needle assemblies comprise a barrel and flanges that are arranged in the same manner with each other. Furthermore, in order to better house a variety of syringe and needle assemblies, the present invention comprises a first clamping jaw 22 and a second clamping jaw 23. The first clamping jaw 22 and the second clamping jaw 23 accommodates the adapter of the syringe and needle assembly. The first clamping jaw 22 is mounted within the first lateral-half portion 4, adjacent to the open end 3. Similarly, the second clamping jaw 23 is mounted within the second lateral-half portion 5, adjacent to the open end 3. This arrangement ensures that the syringe does not escape past the tubular housing 1 as the user engages the plunger 9.

Figure 6:
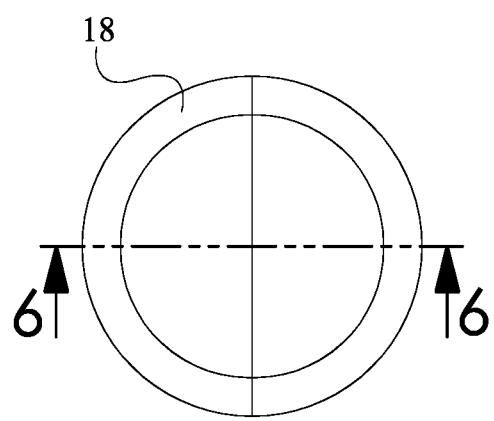
FIG. 6 is a top side view of the present invention.
Figure 7:
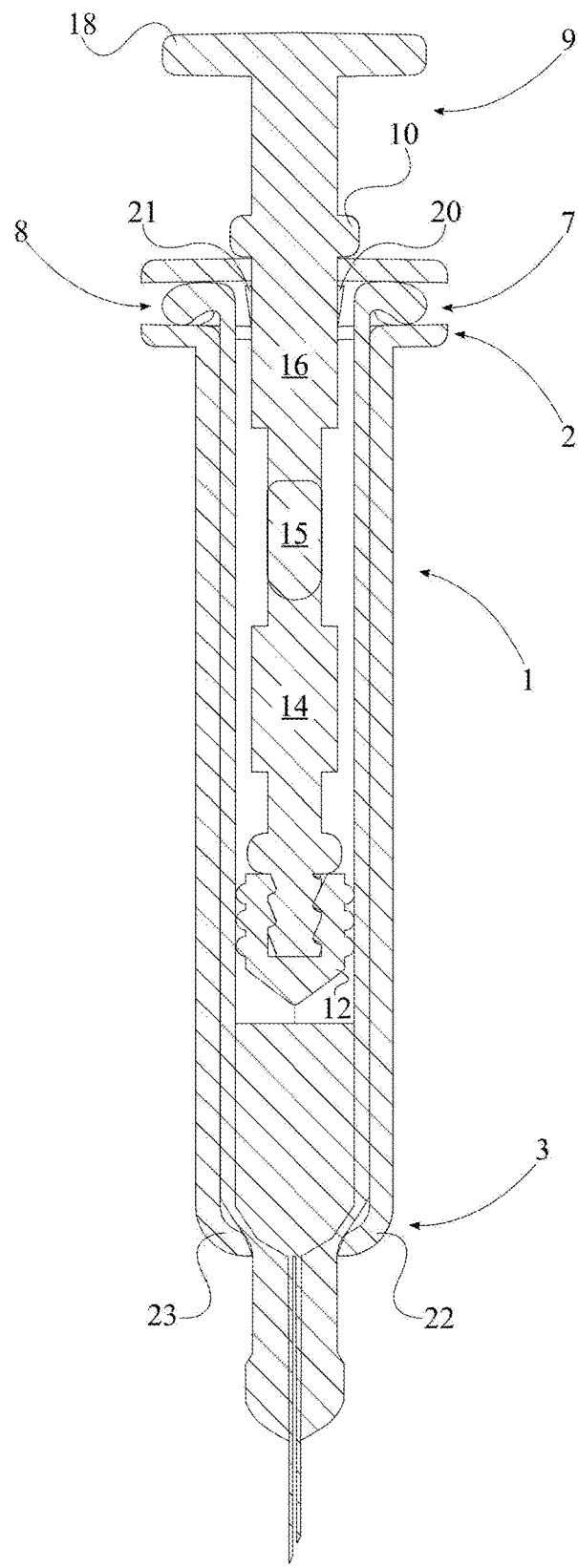
FIG. 7 is a cross-sectional view of the present invention, wherein a syringe is enclosed by the tubular housing while the plunger is locked in place.
Figure 8:
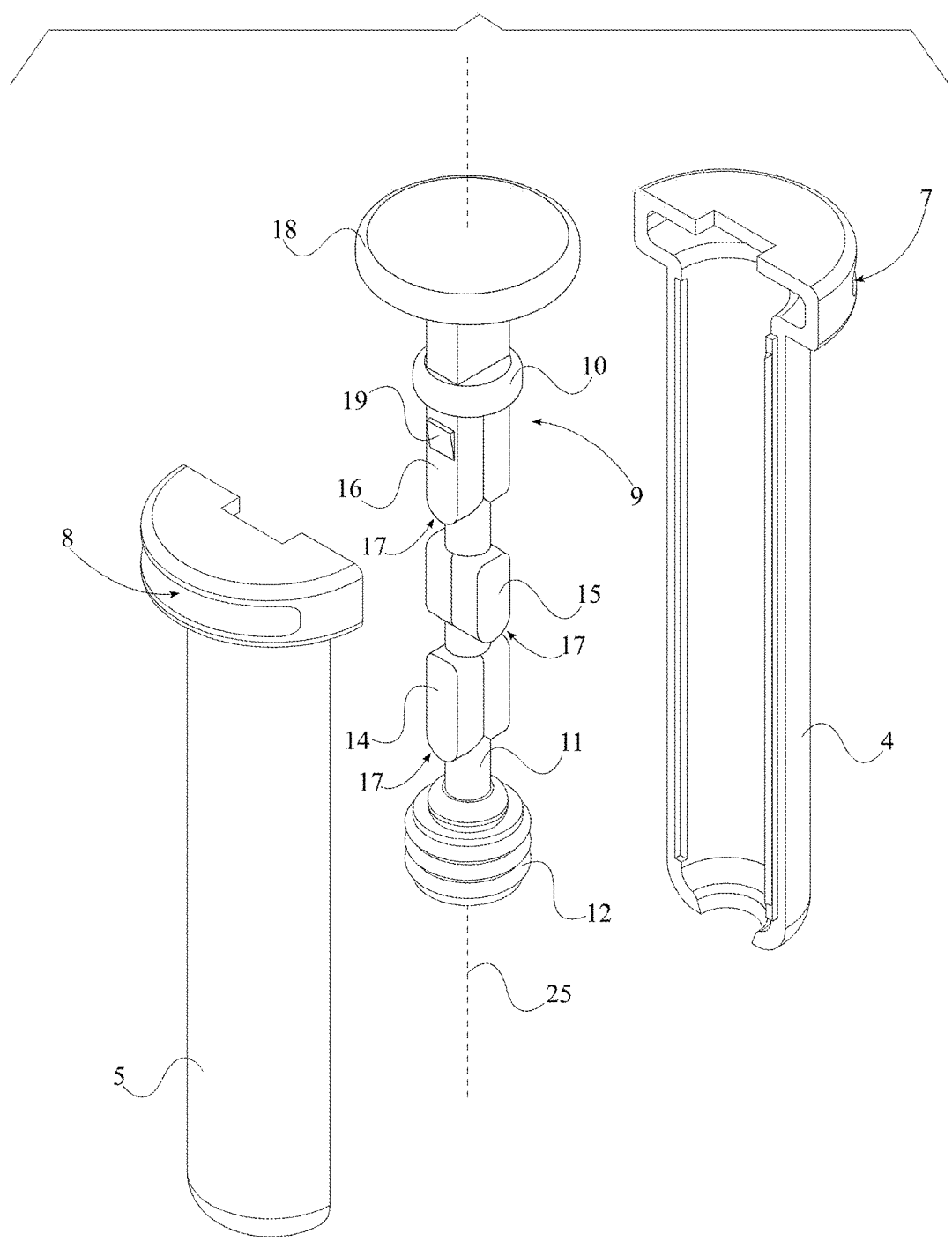
FIG. 8 is an exploded view of the present invention.

In the preferred embodiment of the present invention, the plunger 9 further comprises a knob 18. The knob 18 provides a platform for which a user may force the shaft 11 and sealing body 12 further into the syringe. Furthermore, the knob 18 allows the user to rotate the plunger 9 accordingly, so that the first single dose and the second single dose may be administered. The knob 18 is positioned external to the tubular housing 1 and is terminally connected to the shaft 11, opposite the sealing body 12, as shown in FIG. 6 and FIG. 7. This configuration allows the user to engage the sealing body 12 without contaminating the drug. In order to facilitate the engagement of the knob 18 by the user, the preferred embodiment of the present invention further comprises a grasping flange 24. The grasping flange 24 allows the user to counteract the force of the downward movement of the knob 18. The grasping flange 24 is laterally mounted about the tubular housing 1, adjacent to the closed end 2, in order to enhance the ergonomic structure of the present invention.

Figure 3:
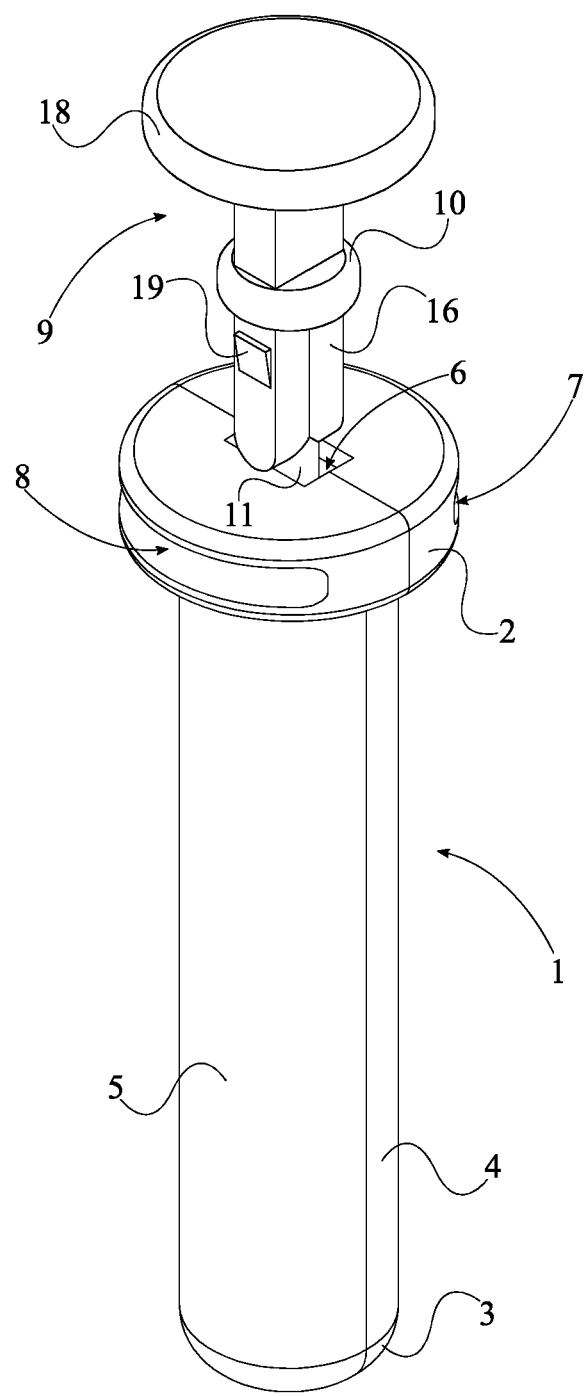
FIG. 3 is a top perspective view of the present invention, wherein the plunger is positioned to release the second dosage from the present invention.

In order to prevent the reuse of the syringe and needle assembly engaged with the present invention, the present invention comprises at least one spring-loaded barb 19. The at least one spring-loaded barb 19 is positioned in between a last bar 13 and the stopper 10, wherein the last bar 13 is one of the plurality of cross bars 13 and is positioned adjacent to the stopper 10, as shown in FIG. 3. This configuration allows the at least one spring-loaded barb 19 to secure the position of the plunger 9 within tubular housing 1 once the second dose is fully expelled from within the syringe. In the preferred embodiment of the present invention, the at least one spring-loaded barb 19 comprises a first spring-loaded barb 20 and a second spring-loaded barb 21, as shown in FIG. 7. The first spring-loaded barb 20 and the second spring-loaded barb 21 effectively secure the position of the plunger 9 within the tubular housing 1. The first spring-loaded barb 20 and the second spring-loaded barb 21 are diametrically opposed to each other about the shaft 11 so that a significant amount of force is required to retract the plunger 9 from the housing, resulting in the damaging or separation of the first lateral half-portion 4 and the second lateral half-portion 5.

Figure 2:
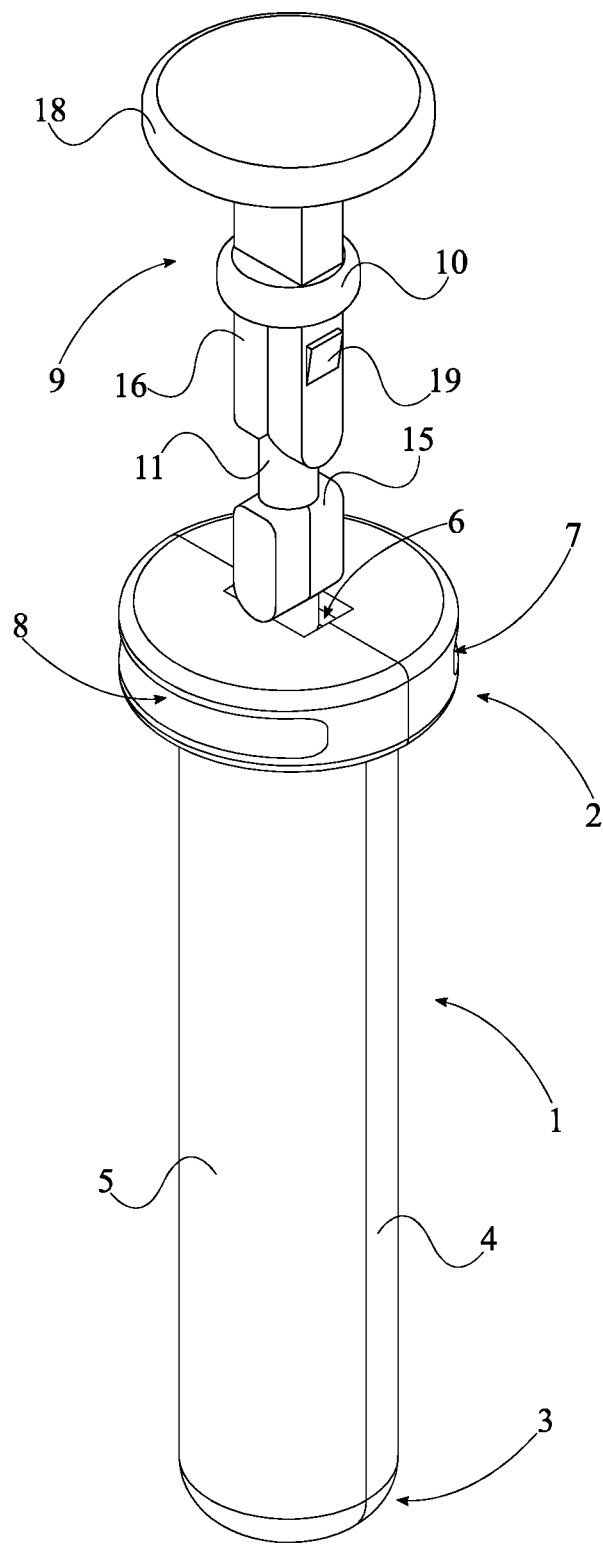
FIG. 2 is a top perspective view of the present invention, wherein the plunger positioned to release the first dosage from the present invention.
Figure 4:
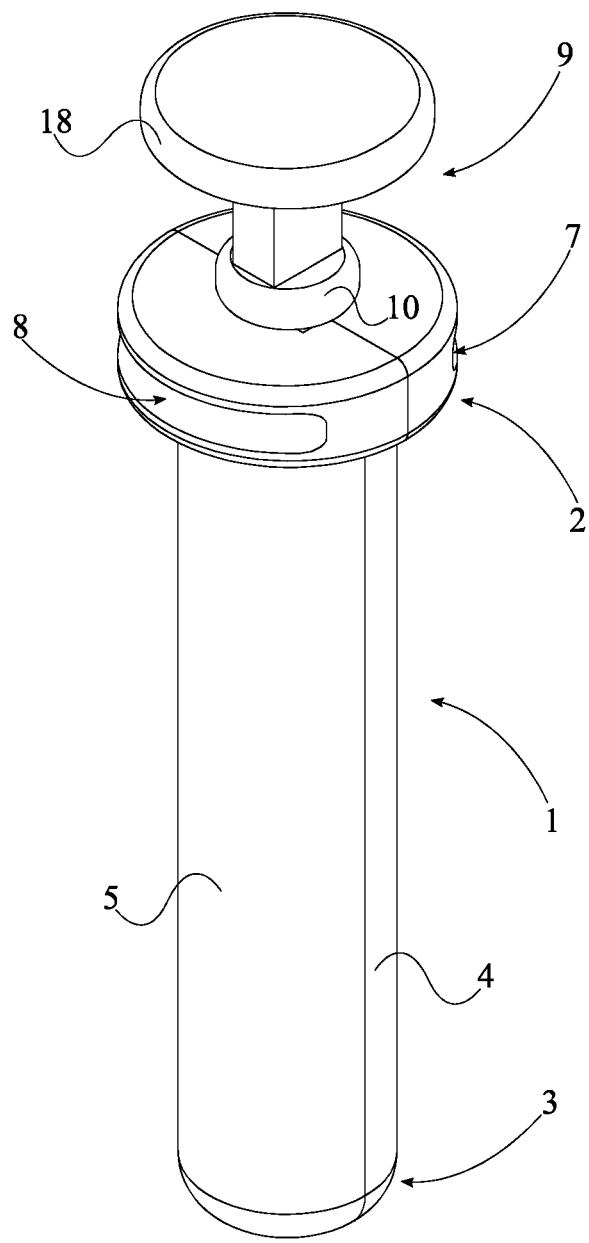
FIG. 4 is a top perspective view of the present invention, wherein the plunger is locked after releasing the first dosage and the second dosage.

In order to deliver two doses, the plurality of cross bars 13 preferably comprises a first cross bar 14, a second cross bar 15, and a third cross bar 16. The first cross bar 14 unlocks the plunger 9, as shown in FIG. 2. The second cross bar 15 prevents no more than a first single dose from being administered to a patient, as shown in FIG. 3, and the third cross bar 16 prevents no more than a second single dose from being administered to a patient, as shown in FIG. 4. The first cross bar 14 is positioned adjacent the sealing body 12, the third cross bar 16 is positioned adjacent the stopper 10, and the second cross bar 15 is positioned between the first cross bar 14 and the third cross bar 16. This arrangement, illustrated in FIG. 7, allows the plunger 9 to expel the correct amount of the first dose and the second dose as the sealing body 12 traverses into the syringe.

Although the invention has been explained in relation to its preferred embodiment, it is to be understood that many other possible modifications and variations can be made without departing from the spirit and scope of the invention as hereinafter claimed.

What is claimed is:

1. A dual-dose syringe system comprising:
   a tubular housing;
   a plunger;
   the tubular housing comprising a closed end, an open end, a first lateral half-portion, a second lateral half-portion, an accommodation space, a key slot, a first grasping flange, a second grasping flange, a first flange-receiving hole and a second flange-receiving hole;
   the plunger comprising a stopper, a shaft, a sealing body and a plurality of cross bars;
   the first lateral half-portion and the second lateral half-portion being detachably attached to each other;
   the accommodation space being formed in between the first lateral half-portion and the second lateral half-portion;
   the key slot penetrating the closed end along a central axis of the tubular housing and being communicated with the accommodation space;
   the shaft being slidably engaged through the key slot;
   the sealing body being positioned within the accommodation space;

the sealing body being terminally connected to the shaft;
the stopper being connected along the shaft;
the stopper being located offset from the sealing body;
each of the plurality of cross bars being connected perpendicular to the shaft;
the plurality of cross bars being distributed along the shaft;
the plurality of cross bars being located in between the sealing body and the stopper;
each of the plurality of cross bars being positioned perpendicular to a corresponding adjacent cross bar among the plurality of cross bars;
the first grasping flange being laterally formed on the first lateral half-portion;
the first grasping flange being located adjacent to the closed end;
the second grasping flange being laterally formed on the second lateral half-portion;
the second grasping flange being located adjacent to the closed end;
the first flange-receiving hole laterally penetrating the first grasping flange and being communicated with the accommodation space;
the second flange-receiving hole laterally penetrating the second grasping flange and being communicated with the accommodation space;
the first flange-receiving hole and the second flange-receiving hole being positioned perpendicular to the central axis;
the first flange-receiving hole and the second flange-receiving hole being diametrically opposed to each other about the tubular housing;
at least one spring-loaded barb;
the at least one spring-loaded barb comprising a first spring-loaded barb and a second spring-loaded barb;
the first spring-loaded barb and the second spring-loaded barb each being laterally mounted to a last cross bar among the plurality of cross bars;
the first spring-loaded barb and the second spring-loaded barb being diametrically opposed to each other about the last cross bar;
the last cross bar being positioned closest to the stopper with respect to remaining cross bars among the plurality of cross bars;
each of the plurality of cross bars comprising a rounded end portion; and
the rounded end portion having a convex contour oriented axially towards the sealing body.

2. The dual-dose syringe system as claimed in claim 1 comprising:
the plunger comprising a knob;
the knob being positioned external to the tubular housing;
the knob being terminally connected to the shaft; and
the knob being located opposite to the sealing body.

3. The dual-dose syringe system as claimed in claim 1 comprising:
the plurality of cross bars being centrally positioned with the shaft; and
the plurality of cross bars and the key slot being coextensive.

4. The dual-dose syringe system as claimed in claim 1 comprising:
the plurality of cross bars comprising a first cross bar, a second cross bar and a third cross bar;
the first cross bar being positioned adjacent to the sealing body;
the third cross bar being positioned adjacent to the stopper; and
the second cross bar being positioned in between the first cross bar and the third cross bar.

5. The dual-dose syringe system as claimed in claim 1 comprising:
a first clamping jaw;
a second clamping jaw;
the first clamping jaw being mounted within the first lateral-half portion;
the first clamping jaw being located adjacent to the open end;
the second clamping jaw being mounted within the second lateral-half portion; and
the second clamping jaw being located adjacent to the open end.

* * * * *